US008512612B2

(12) United States Patent
Kook et al.

(10) Patent No.: US 8,512,612 B2
(45) Date of Patent: Aug. 20, 2013

(54) NANO-FIBERED MEMBRANE FOR WESTERN BLOT AND MANUFACTURING METHOD OF THE SAME

(75) Inventors: Joong Ki Kook, Seoul (KR); Ki Woon Cho, Jeollanam-do (KR); Chan Kim, Gwangju-si (KR); Sang Chul Suh, Seoul (KR); Cheol Hyeon Kim, Seoul (KR); In Yong Seo, Seoul (KR); Seung Hoon Lee, Goyang-si (KR); Yun Hye Kim, Gwangyang-si (KR); Ju Young Park, Gwangju-si (KR)

(73) Assignees: Amomedi Co., Ltd. (KR); Amogreentech Co., Ltd. (KR)

( * ) Notice: Subject to any disclaimer, the term of this patent is extended or adjusted under 35 U.S.C. 154(b) by 324 days.

(21) Appl. No.: 12/893,462

(22) Filed: Sep. 29, 2010

(65) Prior Publication Data

US 2011/0076197 A1 Mar. 31, 2011

(30) Foreign Application Priority Data

Sep. 30, 2009 (KR) .................. 10-2009-0093184
Aug. 16, 2010 (KR) .................. 10-2010-0078667

(51) Int. Cl.
| | |
|---|---|
| *B01D 67/00* | (2006.01) |
| *B01D 24/00* | (2006.01) |
| *B01D 39/00* | (2006.01) |
| *C23C 16/00* | (2006.01) |
| *B29C 67/20* | (2006.01) |
| *B32B 9/04* | (2006.01) |

(52) U.S. Cl.
USPC .............................. 264/175; 264/48; 442/153

(58) Field of Classification Search
USPC ....... 210/505–508, 500.27, 500.36; 442/153, 442/327, 334, 402; 264/175, 448, 48; 422/69; 428/152, 304.4; 427/255.24
See application file for complete search history.

(56) References Cited

U.S. PATENT DOCUMENTS

| 5,690,873 A * | 11/1997 | Harwood et al. ............. 264/103 |
| 7,112,389 B1 * | 9/2006 | Arora et al. .................. 429/128 |
| 7,170,739 B1 * | 1/2007 | Arora et al. .................. 361/502 |
| 8,143,067 B2 * | 3/2012 | Peters et al. .................... 436/86 |
| 2004/0060268 A1 * | 4/2004 | Chung et al. .................... 55/482 |
| 2007/0184256 A1 * | 8/2007 | Okada et al. ............... 428/304.4 |
| 2008/0305389 A1 * | 12/2008 | Arora et al. .................. 429/145 |
| 2009/0123700 A1 * | 5/2009 | Conley et al. ................ 428/152 |
| 2010/0323573 A1 * | 12/2010 | Chu et al. ...................... 442/153 |
| 2011/0042316 A1 * | 2/2011 | Chen et al. .................... 210/650 |
| 2011/0076197 A1 * | 3/2011 | Kook et al. ...................... 422/69 |
| 2012/0091072 A1 * | 4/2012 | Kozlov et al. ................. 210/767 |

* cited by examiner

*Primary Examiner* — Ana Fortuna
(74) *Attorney, Agent, or Firm* — Cantor Colburn LLP (57) ABSTRACT

The present invention relates to a membrane for Western blotting which has a three-dimensional open pore structure, an average pore diameter of 0.1-1.0 µm and a thickness of 30-200 µm, wherein the membrane for Western blotting is manufactured by subjecting nanofibers having an average fiber diameter of 50-1000 nm, obtained by electrospinning, to a hot-plate calendering process, and a method for manufacturing the same. The method comprises the steps of: dissolving a hydrophobic material in a solvent to prepare a spinning solution; subjecting the spinning solution to a spinning process to obtain a hydrophobic polymer nanofiber web; and calendering the obtained nanofiber web to obtain a membrane for Western blotting.

10 Claims, 8 Drawing Sheets

| Treatment time(s) | 0 | 30 | 60 | 180 | 300 |
|---|---|---|---|---|---|
| treated with methanol | | | | | |
| not treated with methanol | | | | | |

NANO-FIBERED MEMBRANE FOR WESTERN BLOT AND MANUFACTURING METHOD OF THE SAME

BACKGROUND OF THE INVENTION

1. Field of the Invention

The present invention relates to a membrane for Western blotting which has a three-dimensional open pore structure, an average pore diameter of 0.1-1.0 µm and a thickness of 30-200 µm, wherein the membrane for Western blotting is manufactured by subjecting nanofibers having an average fiber diameter of 50-1000 nm, obtained by electrospinning, to a hot-plate calendering process, and a method for manufacturing the same.

2. Description of the Prior Art

Membranes for Western blotting which are currently commonly used include porous membranes made of nitrocellulose (NC), nylon or polyvinylidene fluoride (hereinafter referred to as "PVdF") polymers.

Particularly, PVdF-based membranes are mainly used as membranes for Western blotting, because they have excellent protein-binding sensitivity, membrane strength and handling properties compared to nitrocellulose- or nylon-based membranes.

Western blotting is a technique used to detect specific proteins in a given sample of tissue homogenate or extract. It is a technique for detecting any specific protein from a mixture of various proteins and is a method of detecting the presence of a protein by causing an antigen-antibody reaction using an antibody against to the protein to be detected.

Western blotting is also used to separate native gels or denatured proteins by the sizes of the three-dimensional structures of polypeptides or proteins.

In Western blotting, proteins extracted from cells or tissues are mixed with a sample buffer and placed on a molecular sieve made of acrylamide, followed by electrophoresis. Then, the sodium dodecylsulfate (SDS) contained in the sample buffer causes the proteins to carry negative (−) charges, such that the proteins are attracted toward positive (+) charges. At this time, the SDS molecular sieve interferes with the movement of the proteins, so that small molecules move fast, and large molecules move slowly, thus forming bands of various sizes. When a membrane is placed on the gels separated according to size and electricity is applied thereto, the proteins are transferred to the membrane. An antibody against a specific protein to be detected is bound to the membrane, a secondary antibody specific to the antibody is then bound to the membrane, and the resulting color development reactions are imaged by X-rays.

The membrane that is used for this purpose is a porous membrane which is made of a polymer (e.g., PVdF) capable of hydrophobic interaction with protein and has an average pore diameter of 0.2-0.45 µm.

This porous membrane is manufactured by a method such as wet, dry or dry-wet casting by phase separation, wherein a solvent and a polymer are introduced into a nonsolvent such as water. However, the porous membrane is manufactured at a high cost and difficult to manufacture in a large amount.

Also, if the porous membrane is manufactured by phase separation, there is a disadvantage in that the distribution of pore structures is not uniform. For example, a PVdF membrane needs to be subjected to a process of partially hydrophilizing the membrane by immersing it in methanol before use, thereby maximizing the compatibility of the membrane with buffer solution. If this hydrophilizing process is not performed, the sensitivity of the membrane can be reduced, because proteins are not sufficiently adsorbed on the membrane.

This methanol pretreatment process can greatly reduce the strength of the membrane to cause cracks and forms air bubbles to cause a background, thus making it difficult to precisely detect a desired protein.

Accordingly, the present inventors have used an electrospinning process to manufacture a nanofiber membrane which is expensive, manufactured in a simple and convenient manner, has an artificially controllable pore structure, is made of nanofibers having maximized surface area, and has excellent sensitivity compared to existing membranes even when it is not subjected to a methanol pretreatment process, thereby completing the present invention.

SUMMARY OF THE INVENTION

Therefore, it is an object of the present invention to provide a membrane for Western blotting which is manufactured using an electrospinning process, consists of a nanofiber web having maximized surface area so as to allows the need for a methanol pretreatment process to be eliminated, and thus has excellent sensitivity without a background, and a method for manufacturing the same.

Another object of the present invention is to provide a membrane for Western blotting which has more excellent sensitivity as a result of hydrophilizing the membrane by performing plasma surface modification, and a method for manufacturing the same.

To achieve the above objects, according to one aspect of the present invention, there is provided a method for manufacturing a membrane for Western blotting, the method including the steps of: dissolving a hydrophobic polymer material in a solvent to prepare a spinning solution; subjecting the spinning solution to a spinning process to obtain a hydrophobic polymer nanofiber web; and calendering the nanofiber web to obtain a membrane for Western blotting.

The method of the present invention may further include a step of performing surface modification to impart hydrophilicity to the calendered nanofiber web.

The hydrophobic polymer material that is used in the present invention may be one or a mixture of two or more selected from the group consisting of, for example, polyvinylidene fluoride (PVdF), nylon, nitrocellulose, polyurethane (PU), polycarbonate (PC), polystyrene (PS), polylactic acid (PLA), polyacrylonitrile (PAN), polylactic-co-glycolic acid (PLGA), polyethyleneimine (PEI), polypropyleneimine (PPI), polymethylmethacrylate (PMMA), polyvinyl chloride (PVC), polyvinyl acetate (PVAc), and a polystyrene divinylbenzene copolymer.

The solvent that is used in the present invention may be one or more selected from the group consisting of dimethylformamide (DMF), dimethylacetamide (DMAc), tetrahydrofuran (THF), acetone, alcohol, chloroform, dimethyl sulfoxide (DMSO), dichloromethane, acetic acid, formic acid, N-methylpyrrolidone (NMP), fluoroalcohol, and water.

Nanofibers forming the nanofiber web preferably have a diameter of 50-1000 nm.

The spinning process may be any one selected from among electrospinning, electrospray, electroblown spinning, centrifugal electrospinning, flash-electrospinning, bubble electrospinning, melt electrospinning, and needleless electrospinning.

The calendering is carried by any one process selected from among compressing, pressing, hot-plate calendering, rolling, thermal bonding, ultrasonic bonding, a seam sealing tape process, and laminating.

The hydrophobic polymer material is preferably contained in an amount of 5-90 wt % relative to the total weight of the sinning solution.

The calendering step is carried out while performing heat treatment at a temperature between 60° C. and 200° C.

The surface modification is preferably carried out by plasma treatment.

The plasma treatment is carried out using oxygen or argon gas.

The plasma treatment is preferably carried out during 30-300 seconds.

The membrane preferably has an average pore diameter of 0.1-1.0 μm, a thickness of 30-200 μm and a porosity of 60% or more.

According to another aspect, there is provided a membrane for Western blotting which is manufactured according to said method.

DETAILED DESCRIPTION OF THE INVENTION

To manufacture a nanofiber membrane for Western blotting according to the present invention, a hydrophobic polymer, for example, a PVdF polymer, is dissolved in a solvent at a concentration at which it can be spun, thereby preparing a spinning solution. The spinning solution is transferred to a spinneret nozzle and then electrospun by applying high voltage to the nozzle. The nanofiber web manufactured by the electrospinning is subjected to a calendering process, thereby manufacturing a membrane having an average pore diameter of 0.1-1.0 μm, an average fiber diameter of 50-1,000 nm and a thickness of 30-200 μm.

This nanofiber membrane has excellent sensitivity, even when it is not subjected to a methanol pretreatment process, and thus it can be used for the separation and detection of proteins. It may also be subjected to various surface modification processes including plasma treatment to hydrophilize the surface thereof before use.

Hereinafter, each step of the method for manufacturing the nanofiber membrane according to the present invention will be described in detail.

Step of Preparing a Spinning Solution Containing a Hydrophobic Polymer

A hydrophobic polymer (e.g., PVdF) is dissolved in a suitable solvent at a concentration at which it can be spun, thereby preparing a spinning solution. The content of the polymer material (PVdF) in the spinning solution is preferably 5-90 wt %. If the content of the polymer material in the spinning solution is less than 5 wt %, when the spinning solution is electrospun, it will form beads rather than forming nanofibers, thus making it difficult to manufacture a membrane. On the other hand, if the content of the polymer material is more than 90%, it will be difficult to form fibers, because the viscosity of the spinning solution is high. Accordingly, although the preparation of the spinning solution is not specifically limited, it is preferable that the concentration of the polymer in the spinning solution be set at a concentration at which a fibrous structure can be easily formed, thereby controlling the morphology of fibers.

Step of Forming a Polymer Nanofiber Web

The above-prepared spinning solution is transferred to a spin pack using a metering pump, and then electrospun by applying high voltage to the spin pack using a high voltage controller. Herein, the voltage used is adjustable within the range of 0.5 to 100 kV, and as a current collector plate, an electrically conductive metal or release paper may be used and it may be grounded or negatively charged before use. The current collector plate is preferably used together with a suction collector attached thereto in order to facilitate bundling of fibers during spinning.

In the electrospinning, the interval between the spin pack and the current collector plate is preferably controlled to 5-50 cm, and the spinning solution is discharged at a rate of 0.0001-5 cc/hole·min using a metering pump. Also, the electrospinning is preferably carried out at a relative humidity of 30-80% in a chamber whose temperature and humidity can be controlled. The nanofiber web spun as described above has an average fiber diameter of 50-1,000 nm.

The spinning process can be carried out using, in addition to electrospinning, electrospray, electroblown spinning, centrifugal electrospinning, flash-electrospinning, bubble electrospinning, melt electrospinning, or needleless electrospinning.

Step of Calendering the Polymer Nanofiber Web

The above-spun polymer nanofiber web is calendered by various methods, including pressing, compressing, rolling, hot-plate calendering, thermal bonding, ultrasonic bonding, a seam sealing tape method, and laminating, thus obtaining a calendered membrane. Because the obtained polymer nanofiber web has a three-dimensional open pore structure, it can provide a membrane having super-high sensitivity, even when it is not subjected to a methanol pretreatment process.

Herein, the membrane has a thickness of 30-200 μm and an average pore diameter of 0.10-1.0 μm. If the membrane has a thickness of less than 30 μm, it will be difficult to handle due to its low rigidity during Western blotting, and if it has a thickness of more than 200 μm, the production cost will be increased. Also, if the membrane has an average pore diameter of less than 0.1 μm, the post-treatment process cost will be increased and the transfer time will be delayed, and if it has an average pore diameter of more than 1.0 μm, the transfer concentration can be reduced such that precise protein analysis cannot be achieved.

Particularly, when the calendering is carried out, heat treatment may also be carried out simultaneously with the calendering. The heat-treatment temperature in the calendering is preferably in the range of 60 to 200° C. in which the polymer is not melted. If the heat-treatment temperature in the calendaring is lower than 60° C., the bonding between the nanofibers will be unstable such that the separation between the nanofibers will occur, thus making it to perform Western blotting in a suitable manner, and if the heat-treatment temperature is higher than 200° C., the pore structure will be closed by melting of the polymer (e.g., PVdF) constituting the nanofibers, such that proteins cannot be transferred from SDS-PAGE gel to the membrane, thus making it impossible to achieve precise analysis.

Step of Modifying the Surface of Nanofibers

The surface structures of the nanofibers can be modified using various methods, including a chemical method that comprises removing WBL (weak boundary layer) using a solvent, followed by swelling and surface etching; a photochemical modification method that induces a surface reaction by ionization radiations such as X-rays, Y-rays or electron beams; a physical modification method that induces a surface oxidation reaction using corona discharge or high-energy atomic or molecular ions, such as plasma, electron beams or ion beams, under vacuum; and methods that use a flame or ozone.

In the present invention, among such surface modification methods, the plasma treatment method which is most simple while having a low environmental load and excellent surface modification effects is used to hydrophilize the surface of the nanofibers, thereby providing a membrane for ultrahigh-sensitivity Western blotting.

Variables in the plasma treatment process may include the type and flow rate of gas used, treatment pressure, treatment time, electric power, etc. It is preferable to find conditions suitable for the surface modification of the nanofibers.

Namely, oxygen ($O_2$) or argon (Ar) may be used as treatment gas in the plasma treatment process. In the present invention, argon gas having etching and cross-linking effects is preferably used.

The plasma treatment is preferably carried out for 30-300 seconds at a power of 400 W. If the plasma treatment time is shorter than 30 seconds, the degree of hydrophilization of the membrane will be insufficient, and thus when Western blotting is carried out, the membrane will have poor compatibility with buffer solution, and the possibility for a background to occur will be high. If the plasma treatment time is longer than 300 seconds, the membrane will be exposed to plasma for a long period of time, the physical properties of the membrane will be deteriorated, rather than being improved, and the process cost will be increased. The power and the treatment time are inversely proportional to each other, and thus the plasma treatment time can be shortened when the power is increased.

Hereinafter, the present invention will be described in further detail. It is to be understood, however, that these examples are illustrative purposes only and are not to be construed to limit the scope of the present invention.

Example 1

The hydrophobic homopolymer PVdF (HSV 900) was dissolved in the solvent DMAc in an amount of 20 wt % relative to the total weight of the solution, thereby preparing a spinning solution. The spinning solution was transferred to a spinneret nozzle using a metering pump, and then electrospun under the following conditions, thereby obtaining a PVdF nanofiber web: voltage applied: 25 kV; the interval between the spinneret and the current collector: 20 cm; amount discharged per minute: 0.005 cc/g·hole/min; room temperature and atmospheric pressure.

Figure 1:
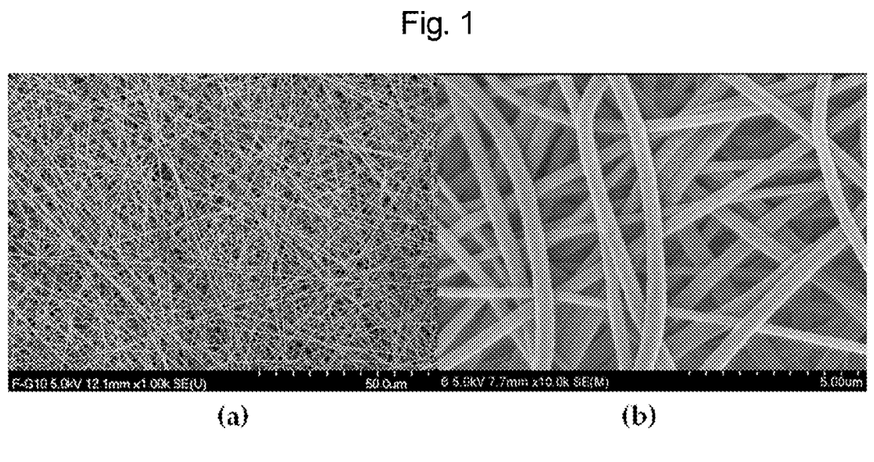
FIG. 1 is a set of scanning electron micrographs of a PVdF membrane manufactured according to Example 1 of the present invention. (a) 1 k× magnification; and (b) 10 k× magnification.

FIG. 1 is a scanning electron micrograph of the spun PVdF nanofiber web. As shown in FIG. 1, the spun nanofibers had an average fiber diameter of about 300-400 nm. Also, the nanofibers had a relatively uniform pore diameter and a three-dimensional open pore structure.

The spun PVdF nanofiber web was calendered by passing it through a hot-plate roll heated to 140° C., thereby manufacturing a PVdF nanofiber membrane. The membrane resulting from the calendering had a thickness of about 80 μm.

Examples 2 and 3

In Examples 2 and 3, the hydrophobic homopolymer PVdF (761) alone (Example 2) or a 50:50 (w/w) mixture of the homopolymer PVdF (761) and the copolymer PVdF (2801) (Example 3) was electrospun in the same manner as Example 1, followed by calendering, thereby obtaining nanofiber membranes. The membranes manufactured in Examples 2 and 3 were subjected to TGA, XRD, SEM and DSC analysis for comparison with a membrane manufactured in Comparative Example. In the results of thermogravimetric analysis (TGA), the samples manufactured in Comparative Example and Examples showed substantially the same results and showed the typical characteristics of the PVdF polymer. These results are described below in the section "structural analysis of the membranes".

Example 4

In Example 4, the PVdF nanofiber membrane manufactured in Example 1 was subjected to surface modification using a plasma cleaner system. The surface modification was carried out for each of 30, 60, 150 and 300 sec at 400 W while supplying 100 sccm of argon.

Figure 2:
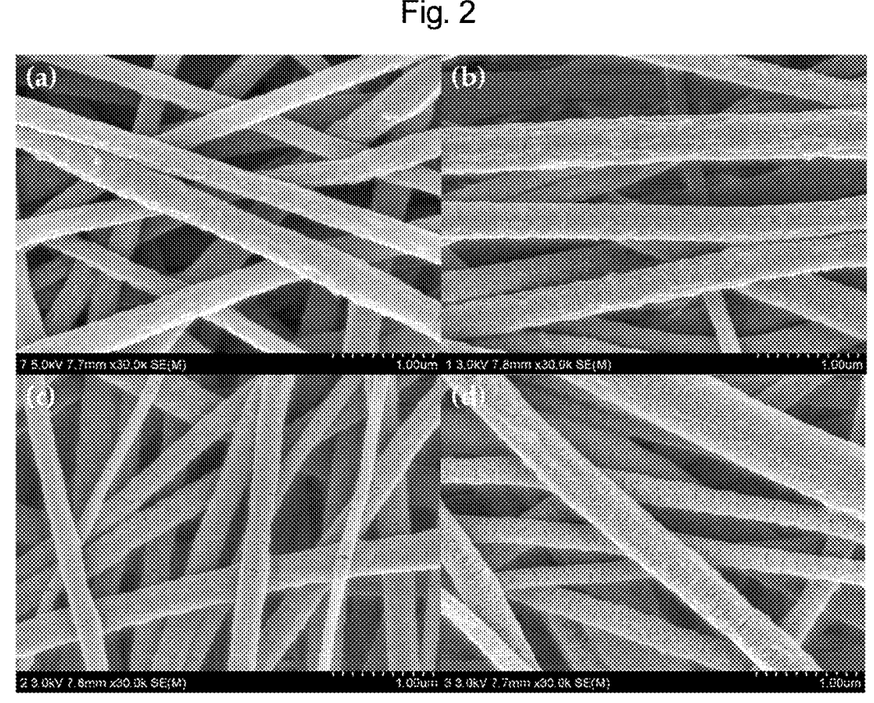
FIG. 2 is a set of scanning electron micrographs of a plasma-treated PVdF membrane manufactured according to Example 4 of the present invention. (a) treated with plasma for 30 seconds; (b) treated with plasma for 60 seconds; (c) treated with plasma for 150 seconds; and (d) treated with plasma for 300 seconds.

FIG. 2 is a set of scanning electron micrographs showing the surface structure of the plasma-treated PVdF membrane of Example 4 according to plasma treatment time. As can be seen in FIG. 2, as the plasma treatment time increased, the size of cracks that occurred on the surface of the PVdF nanofibers increased. This is believed to be because the nanofiber surface was etched due to the plasma treatment.

Figure 3:
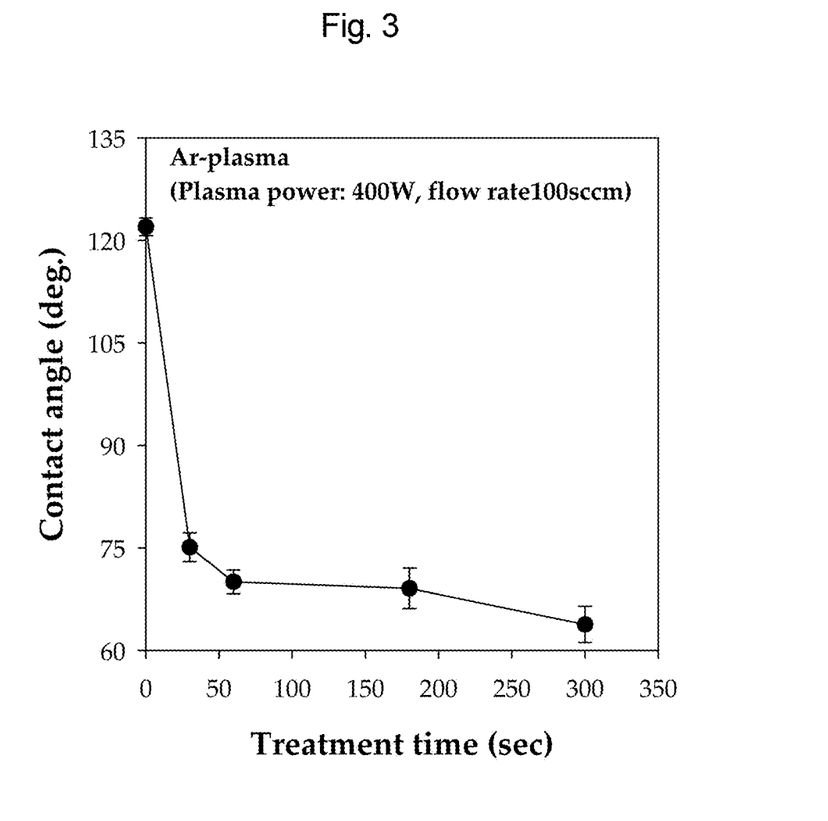
FIGS. 3 and 4 are graphs showing the contact angle and tensile strength of a plasma-treated PVdF membrane manufactured according to Example 4 of the present invention.

FIG. 3 shows the water contact angle of the plasma-treated PVdF membrane of Example 4 according to plasma treatment time. As can be seen in FIG. 3, the water contact angle of the PVdF membrane was decreased due to the plasma treatment. Namely, the membrane showed a hydrophilic nature due to the plasma treatment. As the plasma treatment time increased, the hydrophilic nature of the membrane increased. The change in the hydrophilic nature of the membrane was the greatest when the membrane was plasma-treated for 30 seconds.

Figure 4:
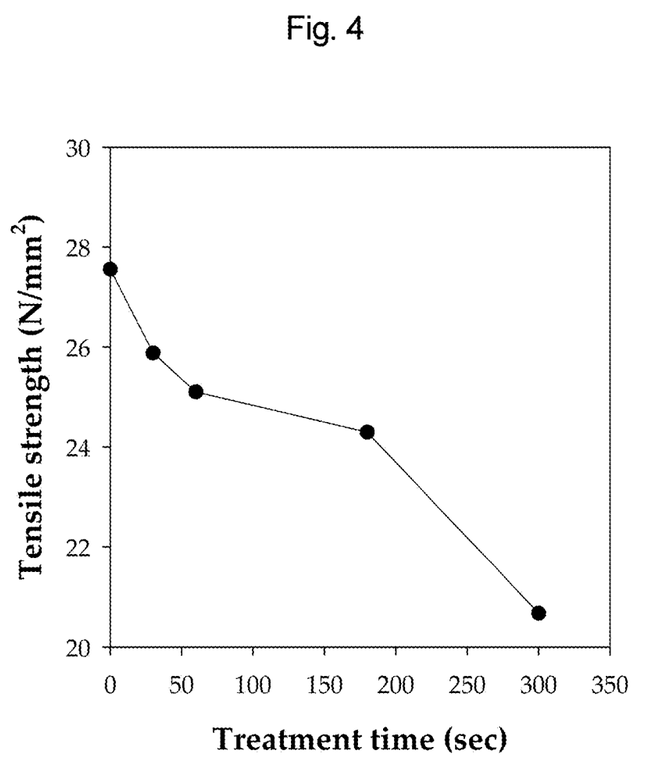

FIG. 4 shows the tensile strength of the plasma-treated PVdF membrane of Example 4 according to plasma treatment time. As can be seen in FIG. 4, as the plasma treatment time increased, the tensile strength showed a tendency to decrease.

This suggests that, as the plasma treatment time increases, the physical properties of the membrane are deteriorated due to the plasma treatment.

Comparative Example

For comparison, a commercially available PVdF membrane (PALL CO., LTD., BioTrace™ PVdF) manufactured by phase separation was used. The PVdF membrane used had a thickness of 150 μm and an average pore diameter of 0.45 μm.

Figure 5:
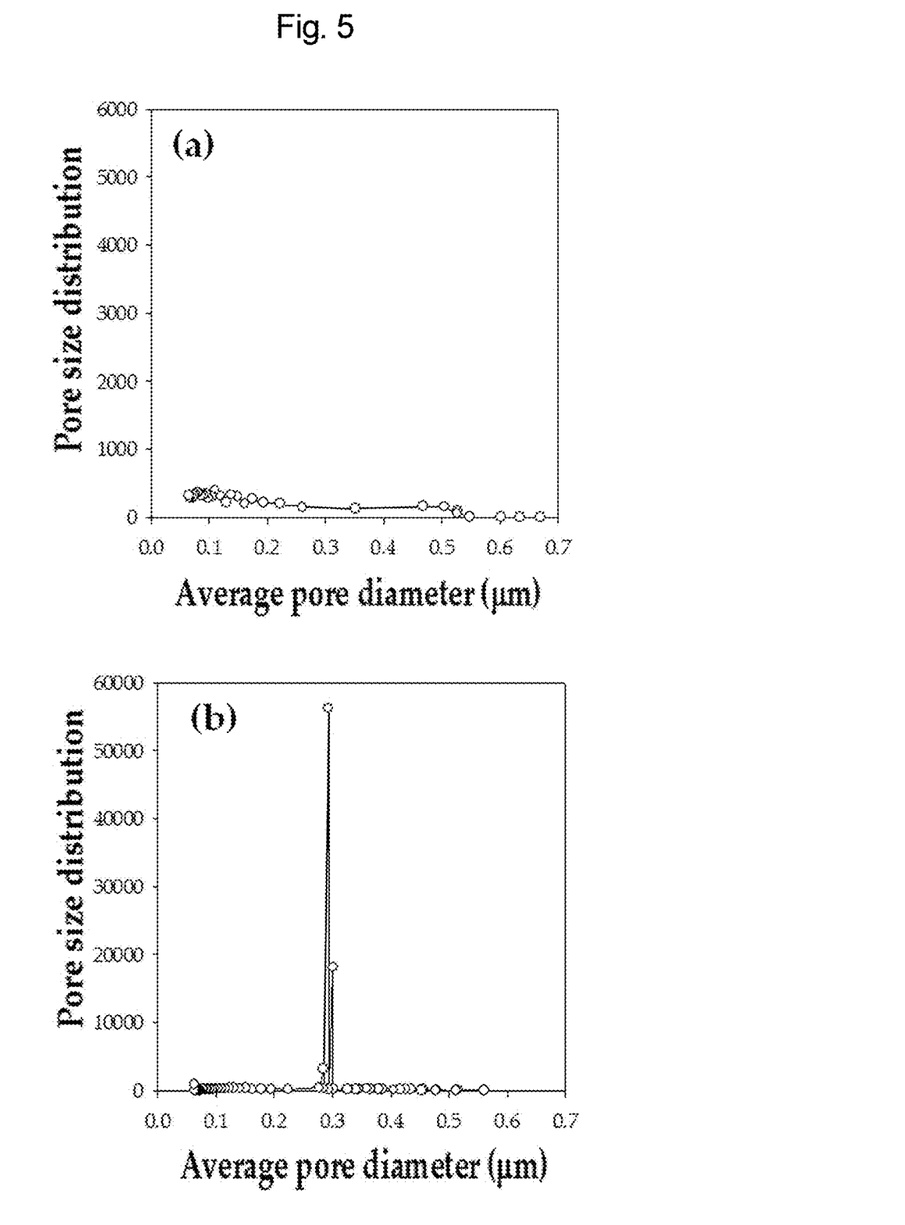
FIG. 5 is a set of graphs showing the size of each of membranes manufactured in Example 1 of the present invention and Comparative Example. (a) Comparative Example; and (b) Example 1.

FIG. 5 shows the average pore diameter of each of the membranes manufactured in Example 1 and Comparative Example, wherein the average pore diameters was measured using a PMI capillary flow porometer. As can be seen in FIG. 5, the nanofiber membrane of Example 1 showed a very uniform average pore diameter (FIG. 5b), whereas the commercial membrane of Comparative Example showed a very non-uniform average pore diameter (FIG. 5a).

Figure 6:
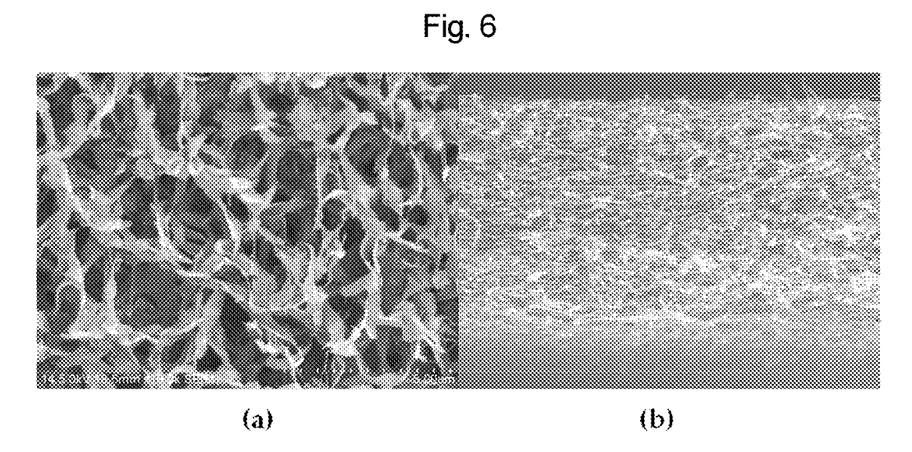
FIG. 6 is a set of scanning electron micrographs of the cross-section of each of membranes manufactured in Example 1 of the present invention and Comparative Example. (a) Comparative Example; and (b) Example 1.

FIG. 6 shows a scanning electron micrograph of the cross-section of each of the membranes in Comparative Example (a) and Example 1 (b).

As shown in FIG. 6(a) for Comparative Example, the commercial membrane had a two-dimensional closed pore structure, because it was manufactured using phase separation. However, as shown in FIG. 6(b) for Example 1, the nanofiber membrane showed a three-dimensional open pore structure when it was manufactured.

(Analysis of Membrane Structure)

The structural analysis of each of the membranes manufactured in Examples 1 to 3 and the commercial membrane manufactured in Comparative Example was carried out by DSC, XRD, TGA and SEM. As can be seen in FIG. 6a, the results of scanning electron micrography (SEM) showed that the membrane of Comparative Example had a non-uniform pore diameter and a closed pore structure.

Figure 7:
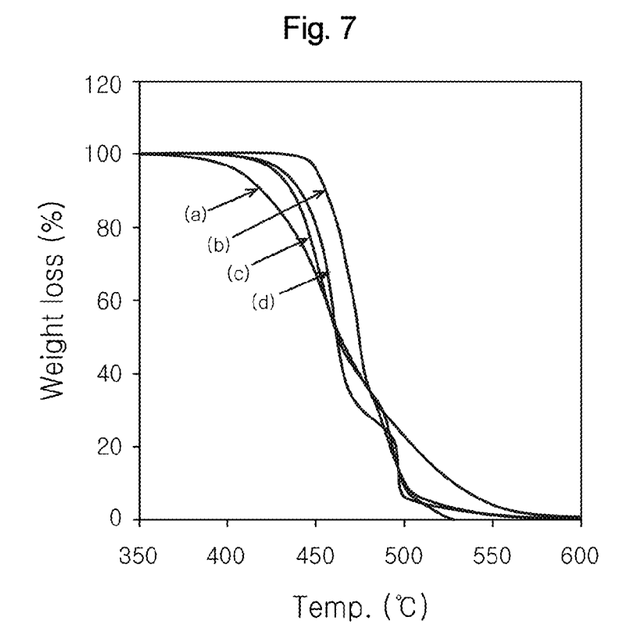
FIG. 7 shows the results of TGA analysis in air of membranes manufactured in Examples of the present invention and Comparative Example. (a) Comparative Example; (b) Example 1 (PVdF HSV 900); (c) Example 2 (PVdF 761); and (d) Example 3 (PVdF 761/2801).

FIG. 7 shows the results of thermogravimetric analysis (TGA) of each of the membranes. As can be seen in FIG. 7, all the commercial membrane of Comparative Example 1 and the membranes of Examples 1 to 3 were not decomposed in air at a temperature of about 500° C. or below. However, it can be seen that the membranes f of Examples 1 to 3 were thermally more stable than the membrane of Comparative Example.

Meanwhile, to determine the porosity of each of the membranes in Example 1 and Comparative Example, a sample of 1 cm (width)×1 cm (length) was taken from each membrane, and the porosity of each sample was measured according to the following equation (1):

$$\text{Porosity}(\%) = \left(\frac{\rho_0 - \rho}{\rho_0}\right) \times 100(\%) \quad (1)$$

wherein $\rho_0$ is the density of PVdF (1.76 g/cm$^3$), and $\rho$ is a measured density value.

The porosity obtained according to the above equation was 73.3% for Example 1, and about 67% for Comparative Example, suggesting that the porosity of the membrane manufactured according to the method of Example 1 was about 10% higher than that of the membrane of Comparative Example.

Test Example 1

Western Blotting

Generally, before Western blotting is carried out, a membrane needs to be partially hydrophilized by treating it with 100% methanol. This is a process of increasing the compatibility of the membrane with Western buffer such that the interaction of the membrane with proteins in gel easily occurs.

In this Test Example, Western blotting was carried out using the membranes of Example 1 and Comparative Example, in a state in which the partial hydrophilization process of the membrane was not carried out.

First, each of the membranes manufactured in Example 1 and Comparative Example was cut to a size of 6 cm (width)×8 cm (length), and then Western blotting was carried out using the cut membranes without treating the membranes with methanol. For this purpose, each of the cut membranes was transferred to 1× transfer buffer and then allowed to stand for 10 minutes. Herein, the transfer buffer contained 3.03 g/L Trisma-base, 14.4 g/L glycine, and 20% methanol (200 ml/L). Gel to be transferred was immersed in transfer buffer for a short time and placed on each membrane, while taking care not to cause bubbles. The gel was brought into close contact with the membrane, 3M paper which has been wet with transfer buffer was applied to both sides of the resulting membrane, and then the membrane was placed in a transfer kit.

The transfer of proteins to the membrane was carried out using a Mini-gel transfer kit at 100 V for 1 hour. At this time, in order to suppress the generation of heat, the transfer was carried out in a state in which the transfer kit was placed on ice. After completion of the transfer, the membrane was separated from the kit and washed with 1×TBST (Tris-buffered saline with 0.05% Tween 20). Herein, the TBST contained 0.2M Tris pH 8 (24.2 g Trisma base) and 1.37M NaCl (80 g NaCl), adjusted to a pH 7.6 by concentrated HCl.

Herein, the purified protein antigen was used at concentrations of 20, 10, 5, 2.5 and 1 μg, and 10% SDS-PAGE gel was used. The total transfer time was about 100 minutes, and the blocking time was 90 minutes.

As a primary antibody, β-actin (Santa cruz, sc-47778) was 5000-fold diluted and allowed to react with the transfer membrane at −4° C. for about one day (24 hrs). The expression of proteins transferred to the membrane was observed using X-ray films.

Figure 8:
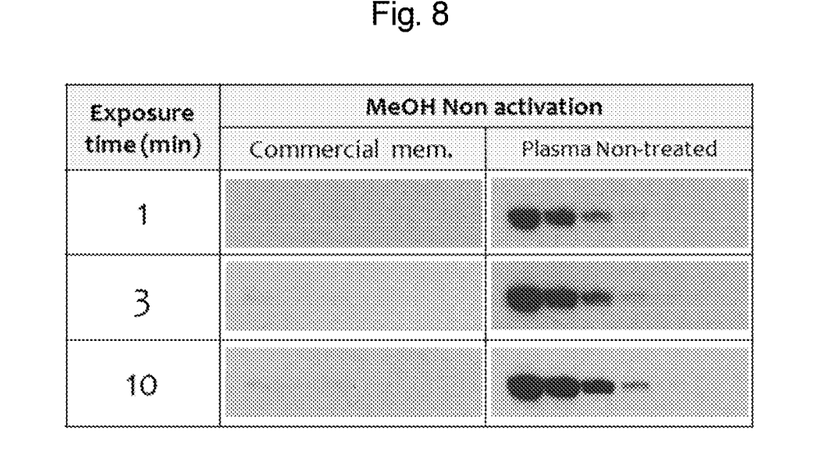
FIG. 8 shows the results of Western blotting conducted using each of membranes manufactured in Example 1 of the present invention and Comparative Example.

FIG. 8 shows the results of performing Western blotting using the membranes manufactured in Example 1 and Comparative Example. As shown in FIG. 8, in the case of the commercial membrane, the expression of protein could not be observed when the membrane was not treated with methanol. However, in the case of the membrane (Plasma Non-treated) of Example 1, the expression of protein was clearly observed. This is because the membrane of Example 1 showed capillary effects, since it had a three-dimensional open pore structure in which the pores extend from one surface to the other surface of the membrane as a result of electrospinning.

Also, it is believed that the membrane of Example 1 had a uniform pore diameter and a large specific surface area resulting from high porosity compared to the membrane of Comparative Example, and thus showed excellent sensitivity. Particularly, because the commercial membrane of Comparative Example was manufactured using phase separation, it is believed that the commercial membrane would necessarily have a two-dimensional closed open structure, and thus would have low sensitivity compared to the nanofiber membrane of Example 1.

Test Example 2

Western Blotting

Using the PVdF nanofiber membranes manufactured in Examples 1 and 4, Western blotting was carried out in the same manner as Test Example 1. Before the Western blotting is carried out, each of the membranes was treated with 100% methanol for 1 min and was treated with plasma for 30 sec, 60 sec, 180 sec or 300 sec or not treated with plasma (plasma treatment time: 0 sec).

Figure 9:
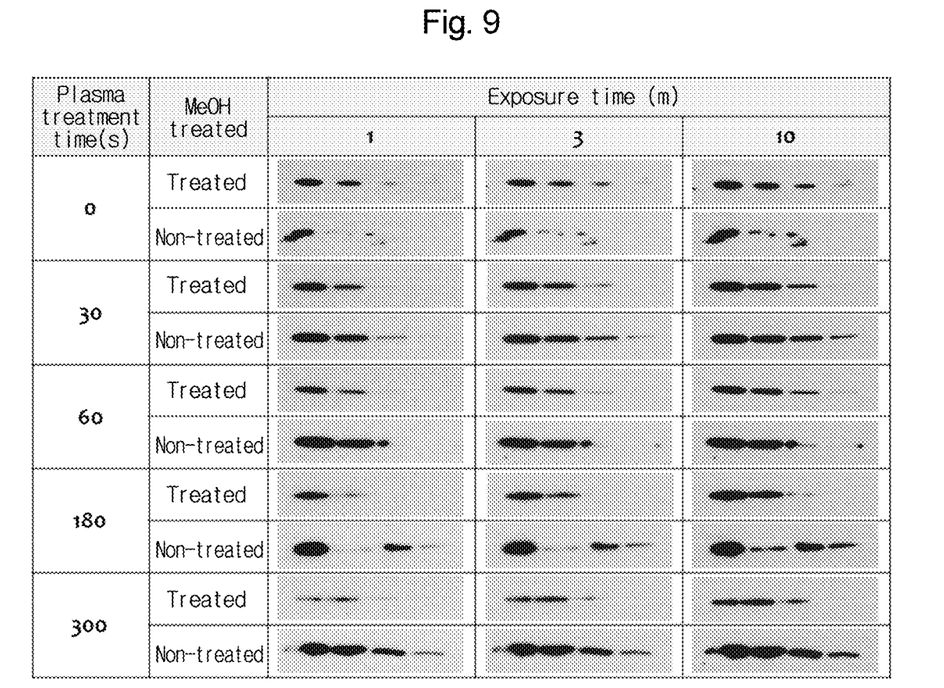
FIGS. 9 and 10 show the results of Western blotting conducted using each of membranes manufactured in Examples 1 and 4 of the present invention.

FIG. 9 shows the results of carrying out Western blotting using each of the membranes manufactured in Examples 1 and 4. As shown in FIG. 9, in the case of the membrane of Example 1 that was not treated with plasma (plasma treatment time: 0 sec), the membrane treated with methanol (MeOH) showed high protein expression compared to the membrane that was not treated with methanol. However, in the case of the membrane of Example 4 treated with plasma for each of 30 sec, 60 sec, 180 sec and 300 sec, the membrane that was not treated with methanol showed high protein expression compared to the membrane treated with methanol. This is believed to be because, when the membrane that has already been surface-hydrophilized by plasma treatment was treated with methanol, the surface hydrophilization became excessive, thus interfering with the hydrophobic interaction between the membrane and the protein.

Test Example 3

Western Blotting

In order to observe the change of the plasma-treated membranes with time, the PVdF nanofiber membranes manufactured in Examples 1 and 4 were allowed to stand at room temperature for 3 months, and then Western blotting was carried out using the membranes in the same manner as Test Examples 1 and 2. The results of Western blotting are shown in FIG. 10.

Figure 10:
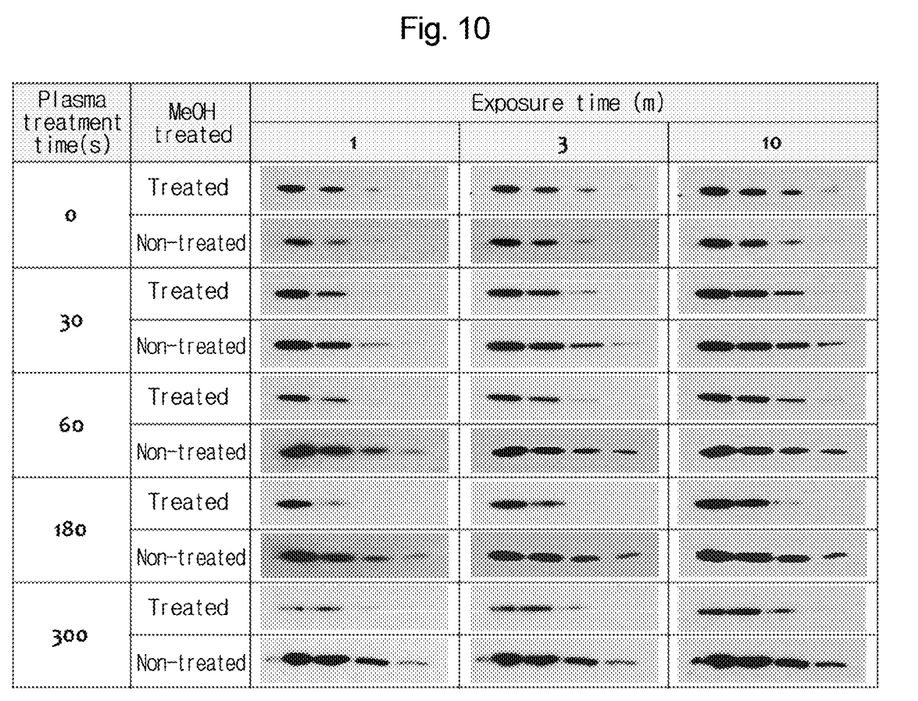

As shown in FIG. 10, the same results as those of Test Example 2 were obtained even 3 months after the membranes have been treated with plasma. This suggests that the surface structure of the nanofibers treated with argon plasma did not significantly change with time.

Figure 11:
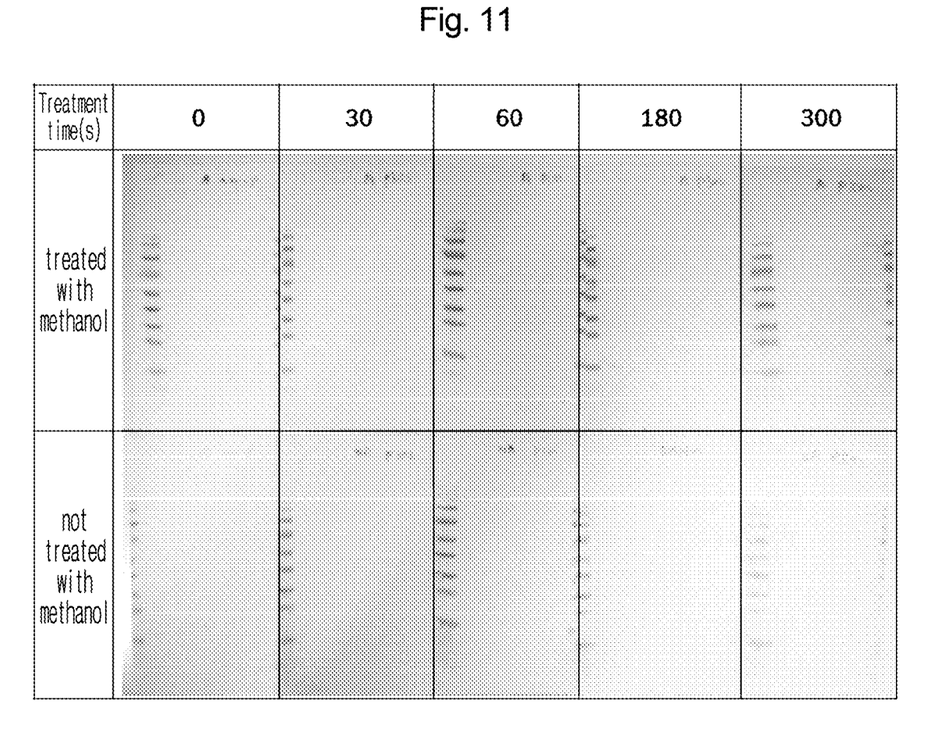
FIG. 11 is a photograph showing the discoloration of membranes after Western blotting.

In the case of Test Examples 2 and 3, when the plasma treatment time was 30 sec, the expression of protein was more clearly observed. As shown in FIG. 11, this is because, when the plasma treatment time was longer than 60 sec, the surface hydrophilization of the membrane became excessive, and thus when Western blotting was carried out, the membrane changed to yellow. This is attributed to the interaction between the membrane and the material contained in the Western blotting buffer, but does not cause a significant problem in performing Western blotting.

Also, as can be seen from the results of FIGS. 9 and 10, the expression of protein was more evident in the case of the sample treated with plasma compared to the case of the sample treated with methanol. This suggests that plasma treatment more uniformly modifies the surface structure of the nanofibers compared to methanol treatment.

Particularly, the nanofiber membrane of the present invention more effectively adsorbed protein compared to the existing commercial membrane. This is believed to be because the nanofibers have a large specific surface area and a capillary effect resulting from its three-dimensional open pore structure. Also, as shown in FIG. 6, this is because the nanofiber membrane has a uniform pore structure compared to the existing commercial membrane.

Accordingly, in the nanofiber membrane of the present invention, protein expression occurs even when the membrane has not been hydrophilized by methanol treatment. Also, when it is hydrophilized by plasma treatment and used as a membrane for Western blotting, it has excellent sensitivity without a background.

As described above, the membrane of the present invention can be used particularly as a membrane for Western blotting. In addition, it can be used as a membrane in various fields, including protein separation, analysis, detection and diagnosis.

Accordingly, the membrane for Western blotting according to the present invention is manufactured by a simple process, and thus can be manufactured in a large amount at a low cost. In addition, it provides excellent sensitivity compared to existing membranes, and thus can be used in various applications, including protein separation, analysis and detection.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for manufacturing a membrane for Western blotting, the method comprising the steps of:
    dissolving a hydrophobic polymer in a solvent to prepare a spinning solution, wherein the hydrophobic polymer is contained in an amount of 5-90 wt % based on the total weight of the spinning solution;
    subjecting the spinning solution to an spinning process to obtain a hydrophobic polymer nanofiber web;
    calendering the obtained nanofiber web to obtain a membrane for Western blotting; and
    plasma-etching a surface of the hydrophobic polymer nanofiber to impart hydrophilicity to the calendered nanofiber web and thereby improve sensitivity of the membrane for Western blotting.

2. The method of claim 1, wherein the hydrophobic polymer material is one or a mixture of two or more selected from the group consisting of polyvinylidene fluoride (PVdF), nylon, nitrocellulose, polyurethane (PU), polycarbonate (PC), polystyrene (PS), polylatic acid (PLA), polyacrylonitrile (PAN), polylactic-co-glycolic acid (PLGA), polyethyleneimine (PEI), polypropyleneimine (PPI), polymethylmethacrylate (PMMA), polyvinylchloride (PVC), polyvinylacetate (PVAc), and a polystyrene divinylbenzene copolymer.

3. The method of claim 1, wherein the solvent is one or more selected from the group consisting of dimethylformamide (DMF), dimethylacetamide (DMAc), tetrahydrofuran (THF), acetone, alcohol, chloroform, dimethyl sulfoxide (DMSO), dichloromethane, acetic acid, formic acid, N-Methylpyrrolidone (NMP), fluoroalcohol, and water.

4. The method of claim 1, wherein nanofibers forming the nanofiber web has a diameter of 50-1000 nm.

5. The method of claim 1, wherein the spinning process is any one selected from among electrospinning, electrospray, electroblown spinning, centrifugal electrospinning, flash-electrospinning, bubble electrospinning, melt electrospinning, and needleless electro spinning.

6. The method of claim 1, wherein the calendering is performed by any one process selected from among compressing, pressing, hot-plate calendering, rolling, thermal bonding, ultrasonic bonding, a seam sealing tape process, and laminating.

7. The method of claim 1, wherein the calendering step is carried out while performing heat treatment at a temperature between 60° C. and 200° C.

8. The method of claim 1, wherein the plasma-etching is carried out using oxygen or argon gas.

9. The method of claim 1, wherein the plasma-etching is carried out for 30-300 seconds.

10. The method of claim 1, wherein the membrane has an average pore diameter of 0.1-1.0 μm, a thickness of 30-200 μm, and a porosity of 60% or more.

* * * * *